US005643901A

United States Patent [19]
Honbo et al.

[11] Patent Number: 5,643,901
[45] Date of Patent: Jul. 1, 1997

[54] MEDICAMENT FOR TREATING IDIOPATHIC THROMBOCYTOPENIC PURPURA

[75] Inventors: Toshiyasu Honbo, Kobe; Hachiro Seno, Kadoma; Michihisa Nishiyama, Ikeda, all of Japan

[73] Assignee: Fujisawa Pharmaceutical Co., Ltd., Osaka, Japan

[21] Appl. No.: 390,815

[22] Filed: Feb. 16, 1995

Related U.S. Application Data

[63] Continuation of Ser. No. 235,239, Apr. 29, 1994, abandoned, which is a continuation of Ser. No. 956,028, filed as PCT/JP91/00768, Jun. 7, 1991, abandoned.

[30] Foreign Application Priority Data

| Jun. 11, 1990 | [GB] | United Kingdom | 9012942 |
| Jun. 11, 1990 | [GB] | United Kingdom | 9012951 |
| Jun. 11, 1990 | [GB] | United Kingdom | 9012952 |
| Jun. 11, 1990 | [GB] | United Kingdom | 9012953 |
| Jun. 11, 1990 | [GB] | United Kingdom | 9012954 |
| Jun. 11, 1990 | [GB] | United Kingdom | 9012955 |
| Jun. 11, 1990 | [GB] | United Kingdom | 9012956 |
| Jun. 11, 1990 | [GB] | United Kingdom | 9012957 |
| Jun. 11, 1990 | [GB] | United Kingdom | 9012958 |
| Jun. 11, 1990 | [GB] | United Kingdom | 9012959 |
| Jun. 11, 1990 | [GB] | United Kingdom | 9012960 |
| Jun. 11, 1990 | [GB] | United Kingdom | 9012961 |
| Aug. 13, 1990 | [GB] | United Kingdom | 9017701 |

[51] Int. Cl.$^6$ .................................................. A61K 31/33
[52] U.S. Cl. .................................................. 514/183
[58] Field of Search .................................................. 514/291

[56] References Cited

U.S. PATENT DOCUMENTS 4,929,611  5/1990  Okuhara et al. ........................ 514/183

FOREIGN PATENT DOCUMENTS

| 0184162 | 6/1986 | European Pat. Off. . |
| 0323042 | 7/1989 | European Pat. Off. . |
| 90/04398 | 5/1990 | WIPO . |

OTHER PUBLICATIONS

Klinische Wochenschrift, vol. 68, (Suppl. XXI):III, 1990, (Pathophysiology and Pharmacotherapy of Autoimmune Diseases, Satellite Symposium, Jul. 29, 1989), Springer–Verlag, D.B.J. Hermann et al: "Drugs in Autoimmune Diseases", pp. 15–25.

The Merck Manual, 15th Edition, 1987, pp. 1038–1043, Merck & Co., Inc., Rahway, NJ, US, also pp. 159–1160.

Immunology Today, vol. 10, No. 1, Jan. 1989, A.W. Thomson: "FK–506—How Much Potential?", pp. 1–32.

Immunology, vol. 69, No. 2, Feb. 1990, K. Yamamoto et al: "Experimental Treatment of Autoimmune MRL–1pr Mice with Immunosuppressive Compound FK506", pp. 222–227.

Current Opinion in Immunology, vol. 2, No. 6, 1990, Current Biology Ltd., St.J. Collier: "Immunosuppressive Drugs", pp. 854–858.

*Primary Examiner*—Kevin E. Weddington
*Attorney, Agent, or Firm*—Oblon, Spivak, McClelland, Maier & Neustadt, P.C.

[57] ABSTRACT

Macrolide compounds such as the FR-900506 and its related compounds are provided for the prevention or treatment of idiopathic thrombocytopenic purpura and Basedow's disease. Composition containing such compounds is also disclosed.

6 Claims, No Drawings

MEDICAMENT FOR TREATING IDIOPATHIC THROMBOCYTOPENIC PURPURA

This application is a Continuation of application Ser. No. 08/235,239, filed on Apr. 29, 1994, now abandoned, which was a Continuation of application Ser. No. 07/956,028, filed on Dec. 10, 1992, now abandoned, filed as International Application No. PCT/JP91/00768 on Jun. 7, 1991.

This invention relates to a new use of macrolide compounds for idiopathic thrombocytopenic purpura and Basedow's disease.

Accordingly, this invention provides a new use of the macrolide compounds for preventing or treating idiopathic thrombocytopenic purpura and Basedow's disease.

Further, this invention provides a prophylactic or therapeutic agent for idiopathic thrombocytopenic purpura and Basedow's disease, which comprises the macrolide compounds.

Still further, this invention provides a method for preventing or treating idiopathic thrombocytopenic purpura and Basedow's disease, which comprises administering said macrolide compounds to mammals.

The macrolide compounds used in this invention are known and disclosed, for example, in European Patent Publication No. 0184162 and International Publication No. WO 89/05304.

Those known macrolide compounds include the fermentation products, such as FR-900506, FR-900520, FR-900523 and FR-900525, isolated from microorganisms belonging to genus Streptomyces, such as Streptomyces tsukubaensis No. 9993 (FERM BP-927) or Streptomyces hygroscopicus subsp. yakushimaensis No. 7238 (FERM BP-928), and their related compounds prepared from these fermentation products.

These macrolide compounds were indicated inter alia for use in the treatment of rejection to transplantation, autoimmune diseases and infectious diseases.

The inventors of this invention have surprisingly found that the macrolide compounds mentioned hereinbelow are useful for preventing or treating idiopathic thrombocytopenic purpura and Basedow's disease.

The macrolide compounds used in this invention can be represented by the following general formula (I).

I wherein each vicinal pair of substituents [$R^1$ and $R^2$], [$R^3$ and $R^4$], [$R^5$ and $R^6$] independently
a) represent two vicinal hydrogen atoms, or
b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH), (H,H) or —CH$_2$O—;

Y represents O, (H,OH), (H,H), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O-alkyl or OCH$_2$OCH$_2$CH$_2$OCH$_3$ or $R^{21}$a is protected hydroxy;

in addition, $R^{20}$a and $R^{21}$a may together represent an oxygen atom in an epoxide ring;

n is 1, 2 or 3;

in addition to their significances above, Y, $R^{10}$ and $R^{23}$, together with the carbon atoms to which they are attached, may represent a 5- or 6- membered N-, S- or O-containing heterocyclic ring, which may be saturated or unsaturated, and which may be substituted by one or more groups selected from alkyl, hydroxy, alkyl substituted by one or more hydroxyl groups, O-alkyl, benzyl and —CH$_2$Se (C$_6$H$_5$).

The specific examples of the definitions of compound (I) and the preferred working modes of the invention are described in detail below.

The term "lower" as used in this specification means, unless otherwise indicated, any number of carbon atoms between 1 and 6, inclusive.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl, butenyl, methylpropenyl, pentenyl, hexenyl, and the like.

Suitable "aryl" may include phenyl, tolyl, xylyl, cumenyl, mesityl, naphthyl, and the like.

Suitable examples of the protective group in the "protected hydroxyl group" may include: 1-(lower alkylthio) (lower)alkyl groups such as lower alkylthiomethyl groups (e.g. methylthiomethyl, ethylthiomethyl, propylthiomethyl, isopropylthiomethyl, butylthiomethyl, isobutylthiomethyl, hexylthiomethyl, etc.), more desirably C$_1$–C$_4$ alkylthiomethyl groups, and most desirably methylthiomethyl; trisubstituted silyl groups such as tri(lower)alkylsilyl groups (e.g. trimethylsilyl, triethylsilyl, tributylsilyl, tert-butyldimethylsilyl, tri-tert-butylsilyl, etc.); lower alkyl-diarylsilyl groups (e.g. methyldiphenylsilyl, ethyldiphenylsilyl, propyldiphenylsilyl, tert-butyldiphenylsilyl, etc.), more desirably tri(C$_1$–C$_4$)alkylsilyl and C$_1$–C$_4$ alkyldiphenylsilyl groups and most desirably tert-butyldimethylsilyl and tert-butyldiphenylsilyl; and acyl groups such as aliphatic acyl groups, aromatic acyl groups and aliphatic acyl groups substituted by aromatic groups, which are derived from carboxylic acids, sulfonic acids or carbamic acids.

The aliphatic acyl group may includes lower alkanoyl groups which may optionally have one or more suitable substituents such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkoxy(lower)alkanoyl groups which may optionally have one or more appropriate substituents such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl groups having one or more suitable substituents such as carboxy or protected carboxy, for example carboxy (lower)alkylcarbamoyl groups( e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl groups such as tri (lower)alkylsilyl(lower)alkoxycarbonyl(lower) alkylcarbamoyl groups(e.g. trimethylsilylmethoxycarbonylethylcarbamoyl, trimethylsilylethoxycarbonylpropyl carbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

The aromatic acyl group may include aroyl groups which may optionally have one or more suitable substituents such as nitro (e.g. benzoyl, toluoyl, xyloyl, naphthoyl, nitrobenzoyl, dinitrobenzoyl, nitronaphthoyl, etc.), arenesulfonyl groups which may optionally have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and so on.

The aromatic group-substituted aliphatic acyl group may include ar(lower)alkanoyl groups which may optionally have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and so on.

Among the above-mentioned acyl groups, the more desirable acyl groups are $C_1$–$C_4$ alkanoyl groups which may optionally be substituted by carboxy, cyclo($C_5$–$C_6$) alkyloxy-($C_1$–$C_4$)alkanoyl groups having two ($C_1$–$C_4$)alkyl groups in the cycloalkyl moiety, camphorsulfonyl, carboxy ($C_1$–$C_4$)alkylcarbamoyl groups, tri($C_1$–$C_4$)alkylsilyl ($C_1$–$C_4$)alkoxycarbonyl($C_1$–$C_4$)alkylcarbamoyl groups, benzoyl which may have one or two nitro groups, halogen-substituted benzenesulfonyl groups, phenyl($C_1$–$C_4$)alkanoyl groups having $C_1$–$C_4$ alkoxy and trihalo($C_1$–$C_4$)alkyl groups. Of these groups, the most desirable are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "5- or 6-membered N-, S- or O-containing heterocyclic ring" may include pyrrolyl, tetrahydrofuryl, and the like.

Preferred embodiments of the Symbols $R^1$ to $R^{10}$, $R^{14}$ to $R^{23}$, X, Y and n are as follows.

$R^1$ and $R^2$ are each hydrogen or combined to form a second bond;

$R^3$ and $R^4$ are combined to form a second bond;

$R^5$ and $R^6$ are combined to form a second bond;

$R^7$ is hydrogen, hydroxy, O-lower alkyl such as methoxy or protected hydroxy;

$R^8$ is hydrogen;

$R^9$ is hydroxy;

$R^{10}$ is methyl, ethyl, propyl or allyl;

$R^{14}$, $R^{15}$, $R^{16}$, $R^{17}$, $R^{18}$ and $R^{19}$ are each methyl;

$R^{20}$ is oxo or [$R^{20}$a,H], wherein $R^{20}$a is hydroxy or methoxy;

$R^{21}$ is [$R^{21}$aH], wherein $R^{21}$a is hydroxy or protected hydroxy;

$R^{23}$ is hydrogen;

X is oxo, (H,OH) or (H,H);

Y is oxo; and n is 1 or 2.

The pharmaceutically acceptable salt of the compound (I) is a nontoxic salt, which may be the corresponding salt with an inorganic or organic base such as alkali metal salts (e.g. sodium salt, potassium salt, etc.), alkaline earth metal salts (e.g. calcium salt, magnesium salt, etc.), ammonium salt and amine salts (e.g. triethylamine salt, N-benzyl-N-methylamine salt, etc.) and so on.

Referring to compound (I), there may exist conformers or one pair or more of stereoisomers such as optical and geometrical isomers due to the asymmetric carbon or the double bond. Such conformers and isomers also fall within the scope of the invention.

Particularly, the most interesting compound is FR-900506 of the following formula.

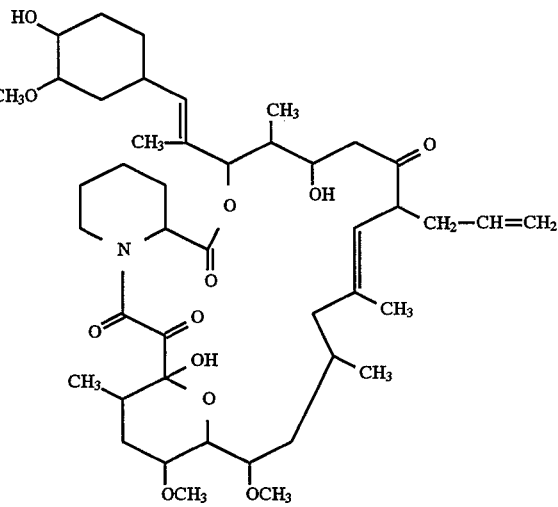

The macrolide compounds of the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external, enteral, intravenous, intramuscular, or parenteral applications. The active ingredient may be compounded, for example, with the usual non-toxic, pharmaceutically acceptable, carriers for tablets, pellets, capsules, suppositories, solutions (saline, for example), emulsion, suspensions (olive oil, for example), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

For applying this composition to a human, it is preferable to apply it by oral, parenteral, external, enteral, intravenous, or intramuscular administration.

While the dosage of therapeutically effective amount of the macrolide compounds varies from and also depends upon the age and condition of each individual patient to be treated, a daily dose of about 0.01–1000 mg, preferably 0.1–500 mg and more preferably 0.5–100 mg. of the active ingredient is generally given for treating diseases, and an average single dose of about 0.2–0.5 mg, 1 mg, 5 mg, 10 mg, 50 mg, 100 mg, 250 mg and 500 mg is generally administered. Daily doses for chronic administration in humans will be in the range of about 0.3 mg/kg/day.

Further, the macrolide compounds (I) used in the present invention are also useful for treating or preventing renal diseases selected from interstitial nephritis, Goodpasture's syndrome, hemolytic-uremic syndrome and diabetic nephropathy; nervous diseases selected from multiple myositis, Guillain-Barré syndrome, Ménière's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjogren's syndrome; adiposis; eosinophilic fasciitis; periodontal disease; muscular dystrophy; and so on.

And further, it is considered that the compounds described in the European Patent Publication Nos. 0349049, 0349061, 0358508, 0364031, 0364032, 0378317, 0378320, 037321, 0388153, 0396399, 0396400, 0399579, 0403242, 0356399, 0402931, 0353678; British Patent Publication No. 2225576; International Patent Application Nos. PCT/GB90/01262 and PCT/JP91/00314; Japanese Patent Application No. 3-53588 (1991), and so on, are also useful for the diseases shown in the present specification.

The following examples are given for the purpose of illustrating the present invention.

EXAMPLE 1

| | |
|---|---|
| FK 506 | 1 g |
| Hydroxypropyl methylcellulose 2910 (TC-5R) | 1 g |
| Lactose | 2 g |
| Croscarmellose sodium (Ac-Di-Sol) | 1 g |

The FK 506 (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK 506 (5 g) (hereinafter, described as SDF). This composition was capsulated by a conventional manner to provide capsules containing 1 mg or 5 mg of FK 506 per each capsule.

EXAMPLE 2

| | 1 mg-Capsule | 5 mg-Capsule |
|---|---|---|
| SDF | 5 mg | 25 mg |
| Lactose | 59.15 mg | 113.6 mg |
| Magnesium stearate | 0.65 mg | 1.4 mg |

The above-mentioned compounds were capsulated by a conventional manner to provide 1 mg- or 5 mg-Capsules respectively, in which SDF was prepared in a similar manner to that of Example 1.

EXAMPLE 3

(1) The solid dispersion composition containing the following compounds were prepared in a similar manner to that of Example 1.

| | |
|---|---|
| FK 506 | 10.0 mg |
| Hydroxypropyl methylcellulose 2910 (TC-5R) | 10.0 mg |
| Lactose | 19.75 mg |
| Croscarmellose sodium (Ac-Di-Sol) | 10.0 mg |

And a tablet was prepared in a conventional manner by using the solid dispersion composition (49.75 mg) mentioned above and magnesium stearate (0.25 mg).

(2) The tablet prepared in (1) was coated with the composition containing the following compounds in a conventional manner.

| | |
|---|---|
| Titanium oxide | 0.85 mg |
| Hydroxypropyl methylcellulose 2910 (TC-5R) | 1.90 mg |
| Macrogol 6000 | 0.25 mg |

We claim:

1. A method for treating idiopathic thrombocytopenic purpura, comprising administering to a mammal in need of such treatment an effective amount of a macrolide compound of formula (I)

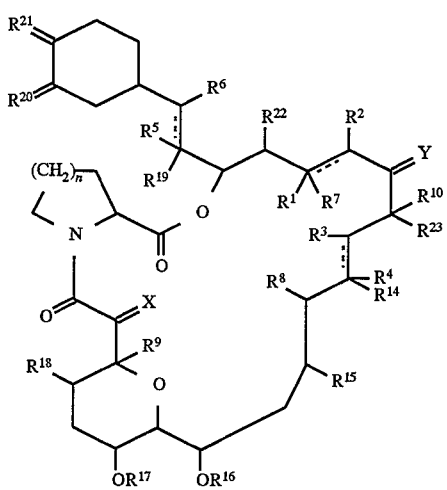

wherein each vicinal pair of substituents $R^1$ and $R^2$, $R^3$ and $R^4$, $R^5$ and $R^6$ independently a) represent two vicinal hydrogen atoms, or
b) form a second bond between the vicinal carbon atoms to which they are attached;

in addition to its significance above, $R^2$ may represent an alkyl group;

$R^7$ represents H, OH, protected hydroxyl or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH), (H,H) or —CH$_2$O—;

Y represents O, (H,OH), (H,H), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O-alkyl or OCH$_2$OCH$_2$CH$_2$OCH$_3$ or $R^{21}$a is protected hydroxy;

in addition, $R^{20}$a and $R^{21}$a may together represent an oxygen atom in an epoxide ring;

n is 1 or 2;

in addition to their significances above, Y, $R^{10}$ and $R^{23}$, together with the carbon atoms to which they are attached, may represent a 5- or 6-membered N-, S- or O-containing heterocyclic ring, which may be saturated or unsaturated, and which may be substituted by one or more groups selected from alkyl, hydroxy, alkyl substituted or by one or more hydroxyl groups, O-alkyl, benzyl and —CH$_2$Se(C$_6$H$_5$);

or a pharmaceutically acceptable salt thereof.

2. The method of claim 1, wherein said macrolide compound is FK506.

3. The method of claim 2, wherein said FK506 is administered at a daily dose of about 0.01–1000 mg.

4. The method of claim 2, wherein said FK506 is administered at a daily dose of about 0.1–500 mg.

5. The method of claim 2, wherein said FK506 is administered at a daily dose of about 0.5–100 mg.

6. The method of claim 2, wherein said FK506 is administered by oral, parenteral, external, enteral, intravenous, or intramuscular administration.

* * * * *